(12) United States Patent
Katayama et al.

(10) Patent No.: US 11,256,963 B2
(45) Date of Patent: Feb. 22, 2022

(54) SURGICAL INSTRUMENT DETECTION SYSTEM AND COMPUTER PROGRAM

(71) Applicant: EIZO Corporation, Ishikawa (JP)

(72) Inventors: Takuya Katayama, Hyogo (JP); Nobuaki Sugii, Hyogo (JP)

(73) Assignee: EIZO Corporation, Ishikawa (JP)

( * ) Notice: Subject to any disclaimer, the term of this patent is extended or adjusted under 35 U.S.C. 154(b) by 120 days.

(21) Appl. No.: 16/617,742

(22) PCT Filed: May 30, 2018

(86) PCT No.: PCT/JP2018/020782
§ 371 (c)(1),
(2) Date: Nov. 27, 2019

(87) PCT Pub. No.: WO2018/221599
PCT Pub. Date: Dec. 6, 2018

(65) Prior Publication Data
US 2020/0193241 A1  Jun. 18, 2020

(30) Foreign Application Priority Data

May 31, 2017 (JP) .............................. JP2017-107892

(51) Int. Cl.
*G06K 9/62* (2006.01)
*G06K 9/34* (2006.01)
(Continued)

(52) U.S. Cl.
CPC ............ *G06K 9/6267* (2013.01); *A61B 34/20* (2016.02); *A61B 34/25* (2016.02); *G06K 9/342* (2013.01);
(Continued)

(58) Field of Classification Search
None
See application file for complete search history.

(56) References Cited

U.S. PATENT DOCUMENTS 5,610,811 A    3/1997  Honda
8,631,489 B2 *  1/2014  Antonakakis ....... H04L 63/1408
                                                 726/22
(Continued)

FOREIGN PATENT DOCUMENTS

EP        3438934 A1 *  2/2019  ............. G06T 7/269
JP     H06-142105 A     5/1994
(Continued)

OTHER PUBLICATIONS

Liu, X. H., Hsieh, C. H., Lee, J. D., Lee, S. T., & Wu, C. T. (Jun. 2014). A vision-based surgical instruments classification system. In 2014 International Conference on Advanced Robotics and Intelligent Systems (ARIS) (pp. 72-77). IEEE. (Year: 2014).*

(Continued)

*Primary Examiner* — Michelle M Entezari
(74) *Attorney, Agent, or Firm* — Maier & Maier, PLLC

(57) ABSTRACT

A surgical instrument detection system is provided that can determine the kinds of surgical instruments without special processing, such as application of an optically readable symbol, to the surgical instruments. A surgical instrument detection system 100 includes: an image input section 31 to input an image taken by a camera 1; an object extraction section 32 to clip an object image of a small steel article from the input image; a determination section 33 to input the object image to a learned classification model 331 and determine a kind of the small steel article based on features included in the object image; and an output image generation section 34 to generate an image representing the result of determination by the determination section and output such image to a monitor 2.

8 Claims, 11 Drawing Sheets

(51) Int. Cl.
*G06K 9/46* (2006.01)
*A61B 34/20* (2016.01)
*A61B 34/00* (2016.01)
*A61B 17/28* (2006.01)

(52) U.S. Cl.
CPC ......... *G06K 9/4652* (2013.01); *G06K 9/6202*
(2013.01); *A61B 17/28* (2013.01); *A61B 2034/2055* (2016.02); *A61B 2034/2065* (2016.02); *G06K 2209/057* (2013.01)

(56) References Cited

U.S. PATENT DOCUMENTS

| | | | | |
|---|---|---|---|---|
| 10,019,654 | B1* | 7/2018 | Pisoni | G06N 3/084 |
| 10,930,395 | B2* | 2/2021 | Mowery | G06N 3/08 |
| 2002/0012467 | A1* | 1/2002 | Shiratani | G06K 9/66 382/224 |
| 2005/0163359 | A1* | 7/2005 | Murao | G01N 15/1475 382/128 |
| 2007/0225550 | A1* | 9/2007 | Gattani | A61B 90/36 600/101 |
| 2014/0081659 | A1* | 3/2014 | Nawana | A61B 5/1118 705/3 |
| 2014/0108086 | A1* | 4/2014 | Prieto | G01N 15/12 705/7.23 |
| 2014/0160264 | A1* | 6/2014 | Taylor | G02B 21/008 348/79 |
| 2014/0198234 | A1* | 7/2014 | Kobayashi | H04N 1/32144 348/231.99 |
| 2015/0003704 | A1 | 1/2015 | Nomura et al. | |
| 2015/0177598 | A1 | 6/2015 | Mima et al. | |
| 2015/0181153 | A1 | 6/2015 | Mima et al. | |
| 2015/0193698 | A1* | 7/2015 | Nakamura | G06N 20/00 706/12 |
| 2016/0287337 | A1* | 10/2016 | Aram | G16H 20/40 |
| 2017/0132785 | A1* | 5/2017 | Wshah | G06N 3/0454 |
| 2017/0161477 | A1* | 6/2017 | Liu | H04L 63/12 |
| 2018/0078315 | A1* | 3/2018 | Ren | A61B 3/1025 |
| 2018/0144466 | A1* | 5/2018 | Hsieh | G06N 3/04 |
| 2018/0168741 | A1* | 6/2018 | Swayze | A61B 90/361 |
| 2018/0182373 | A1* | 6/2018 | Almudafar-Depeyrot | G10L 13/00 |
| 2018/0300576 | A1* | 10/2018 | Dalyac | G06K 9/6218 |
| 2018/0330273 | A1* | 11/2018 | Hu | G06N 20/00 |
| 2019/0053857 | A1* | 2/2019 | Sugie | A61B 1/042 |
| 2019/0056498 | A1* | 2/2019 | Sonn | G01S 17/931 |

FOREIGN PATENT DOCUMENTS

| | | |
|---|---|---|
| WO | 2013/115093 A1 | 8/2013 |
| WO | 2015/001807 A1 | 1/2015 |

OTHER PUBLICATIONS

Rivas-Blanco I, Pérez-Del-Pulgar CJ, García-Morales I, Muñoz VF. A Review on Deep Learning in Minimally Invasive Surgery. IEEE Access. Mar. 24, 2021;9:48658-78. (Year: 2021).*

Su H, Qi W, Yang C, Sandoval J, Ferrigno G, De Momi E. Deep neural network approach in robot tool dynamics identification for bilateral teleoperation. IEEE Robotics and Automation Letters. Feb. 17, 2020;5(2):2943-9. (Year: 2020).*

International Search Report dated Aug. 14, 2018 in corresponding International Application No. PCT/JP2018/020782; 1 pg.

Search Report dated Apr. 22, 2020 in corresponding European Application No. 18808728.2; 5 pages.

Liu et al., "A Vision-based Surgical Instruments Classification System", 2014 International Conference on Advanced Robotics and Intelligent Systems (ARIS 2014), Jun. 6-8, 2014, pp. 72-77.

Tan et al., "A New Method of Surgical Instruments Automatic Identification and Counting", 2011 4th International Congress on Image and Signal Processing, Oct. 15, 2011, pp. 1797-1800.

\* cited by examiner

SURGICAL INSTRUMENT DETECTION SYSTEM AND COMPUTER PROGRAM

TECHNICAL FIELD

The present invention relates to a system to detect a surgical instrument used in surgery and the like.

BACKGROUND ART

Many surgical instruments, such as forceps and tweezers, are used in surgery. Since leaving a surgical instrument in the patient's body during surgery is medical malpractice that should not occur, it is thoroughly ensured that the kind and number of surgical instruments are counted before surgery and whether all surgical instruments are complete is checked after surgery.

However, surgical instruments come in a wide variety of kinds and many of them look very alike only with a slight difference in shape and size. It is thus difficult even for an experienced nurse to accurately distinguish the kinds of surgical instruments by visual observation.

A surgical appliance preparation system is conventionally proposed that can identify the kinds of surgical appliances (including small steel articles) using optically readable symbols, such as bar codes, given to the surgical appliances (PTL 1). It should be noted that the surgical appliance preparation system disclosed in PTL 1 is used for preparation of surgical appliances used in surgery before surgery and is not to check whether the surgical appliances are complete after surgery.

CITATION LIST

Patent Literature

PTL 1: JP 6-142105A

SUMMARY OF INVENTION

Technical Problem

However, giving such an optically readable symbol to each surgical instrument requires special processing, causing an increase in production costs of the surgical instruments. It also takes time and effort for reading the symbol from each surgical instrument with a reader.

It is an object of the present invention to provide a surgical instrument detection system that can readily identify the kinds and number of diverse surgical instruments without special processing, such as application of an optically readable symbol, to the surgical instruments.

Solution to Problem

To solve the above problems, a surgical instrument detection system according to the present invention includes: an image input section to input an image taken by a camera; an object extraction section to clip an object image of a surgical instrument from the input image; a determination section to input the object image to a learned classification model and determine a kind of the surgical instrument based on features included in the object image; and an output image generation section to generate an image representing the result of determination by the determination section and output such image to a monitor.

Advantageous Effects of Invention

According to the above configuration, it is possible to provide a surgical instrument detection system that can readily identify the kinds and number of diverse surgical instruments without special processing, such as application of an optically readable symbol, to the surgical instruments.

DESCRIPTION OF EMBODIMENTS

Figure 1:
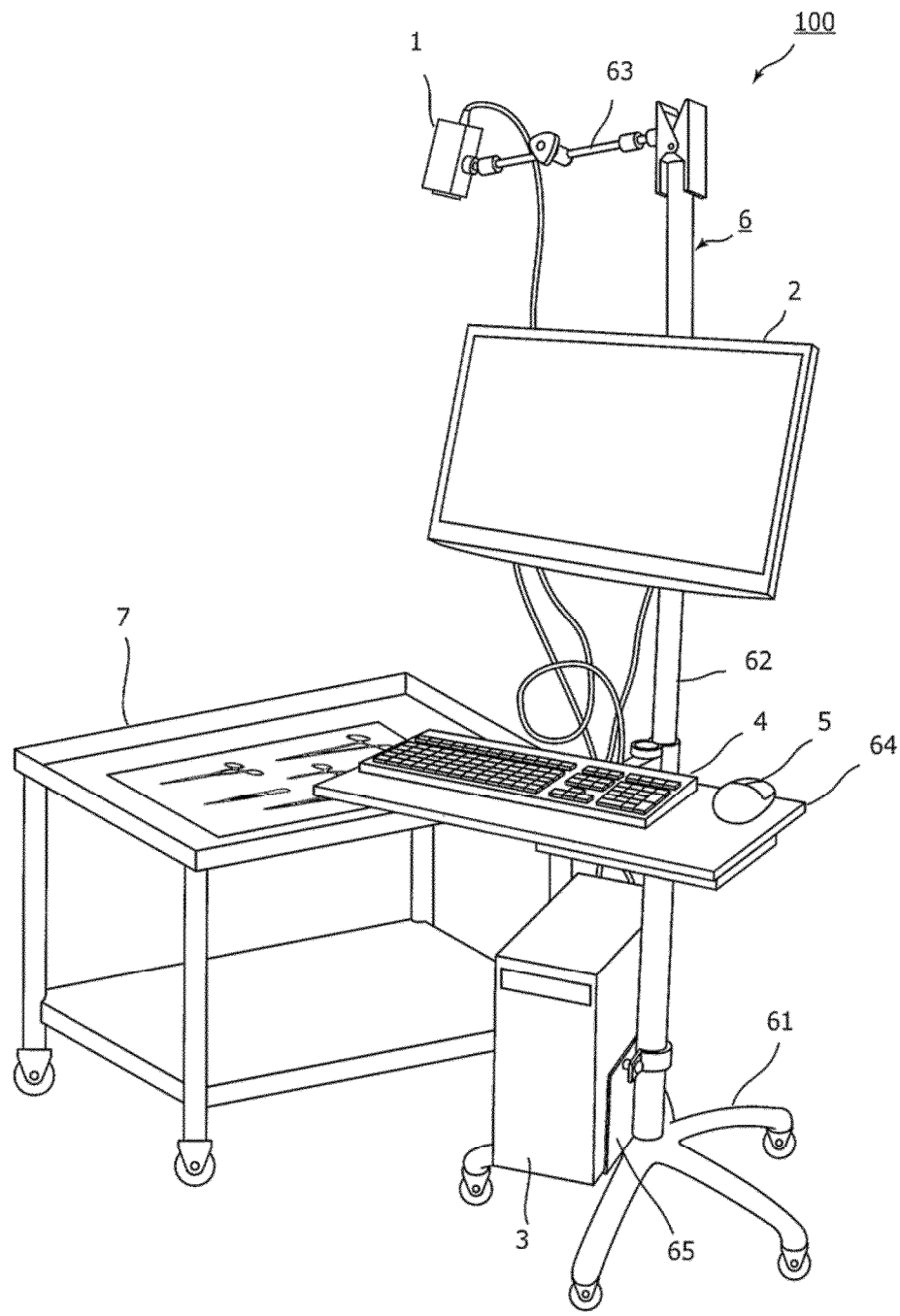
FIG. 1 is a diagram illustrating an overview of a hardware configuration of a surgical instrument detection system according to a first embodiment.

A surgical instrument detection system in a first configuration of the present invention includes:

an image input section to input an image taken by a camera;

an object extraction section to clip an object image of a surgical instrument from the input image;

a determination section to input the object image to a learned classification model and determine a kind of the surgical instrument based on features included in the object image; and an output image generation section to generate an image representing the result of determination by the determination section and output such image to a monitor.

According to the first configuration, it is possible to clip the object image of the surgical instrument from the image taken by the camera and determine the kind of the surgical instrument using the learned model. This allows automatic determination of the kind of the surgical instrument without applying special processing to the surgical instrument.

A second configuration includes the first configuration, in which the output image generation section outputs an image representing the kind of the surgical instrument overlaid on the object image in the taken image.

According to the second configuration, it is possible to readily recognize what sort of surgical instrument each object image is on the monitor.

A third configuration includes the first or second configuration, in which the object extraction section clips the object image based on comparison of a color space vector for each pixel in a background image and the taken image.

Although the background image has to be obtained in advance, the third configuration can clip the object image without depending on the background.

A fourth configuration includes any one of the first and second configurations, in which the object extraction section inputs the taken image to a learned object extraction model and clips the object image based on features included in the taken image.

In the fourth configuration, object extraction is learned in a plurality of lighting conditions in advance, thereby allowing automatic clipping of the object image not affected by the lighting conditions, such as shades and color temperatures.

A fifth configuration includes any one of the first and second configurations, in which the object extraction section converts pixel data of the taken image to data in an HSV color space and clips the object image based on edge information on hue and saturation.

According to the fifth configuration, it is possible to clip the object image not affected by the lighting conditions because hue and saturation are less likely to be affected by shades in comparison with brightness and an environmental change affecting the whole, such as a change in color temperature, does not affect the edges.

A sixth configuration includes any one of the first to fifth configurations, in which the system further includes a comparison section to compare the kinds and number of surgical instruments after surgery with the kinds and number of surgical instruments before surgery, wherein the output image generation section generates an image representing the result of comparison by the comparison section and outputs such image to the monitor.

According to the sixth configuration, it is possible to compare the kinds and number of surgical instruments after surgery with those before surgery, allowing effective prevention of medical accidents of leaving a surgical instrument in the patient's body during surgery.

A computer program as an aspect of the present invention causing a processor of a computer to execute surgical instrument detection, wherein the surgical instrument detection includes instructions for:

inputting an image taken by a camera;

clipping an object image of a surgical instrument from the input image;

determining, by inputting the object image to a learned classification model, a kind of the surgical instrument based on features included in the object image; and generating an image representing the result of determination and outputting such image to a monitor.

A surgical instrument detection method as an aspect of the present invention executed by a processor of a computer, the method including:

inputting an image taken by a camera;

clipping an object image of a surgical instrument from the input image;

determining, by inputting the object image to a learned classification model, a kind of the surgical instrument based on features included in the object image; and generating an image representing the result of determination and outputting such image to a monitor.

EMBODIMENTS

A detailed description is given below to embodiments of the present invention with reference to the drawings. An identical reference sign is given to identical or equivalent parts in the drawings to omit repetitive descriptions. To facilitate the understanding of the description, the drawings referred below may be illustrated in a simplified or schematic configuration or may have omitted components. The scale ratio of the components illustrated in each drawing does not have to reflect the actual scale ratio.

First Embodiment

The first embodiment is described below.

FIG. 1 illustrates an overview of the hardware configuration of a surgical instrument detection system according to the first embodiment. A surgical instrument detection system 100 according to the present embodiment is a small steel article detection system to particularly detect small steel articles among surgical instruments and includes, as illustrated in FIG. 1, a camera 1, a monitor 2, a computer 3, a keyboard 4, and a mouse 5.

The camera 1, the monitor 2, the keyboard 4, and the mouse 5 are connected to the computer 3. Although FIG. 1 exemplifies a configuration provided with the keyboard 4 and the mouse 5, it is possible to omit the keyboard 4 and the mouse 5 by using a monitor allowing touch screen input. Alternatively, a computer may be used that includes a microphone instead of the keyboard 4 and the mouse 5 to accept directions from a user by voice input.

The camera 1, the monitor 2, and the computer 3 are mounted on a cart 6. The cart 6 is provided with legs 61 having wheels. The cart 6 has a pole 62 with an arm 63 mounted on a tip end, and the arm 63 holds the camera 1. The arm 63 desirably has two or more rotation axes to freely adjust the field of view of the camera 1. The cart 6 further includes a table 64 on which the keyboard 4 and the mouse 5 can be placed. The cart 6 further includes a computer support bench 65 on which the computer 3 can be installed.

The surgical instrument detection system 100 having the above configuration can be moved by pushing the cart 6 and is brought into an operating room and the like to photograph, as illustrated in FIG. 1, an instrument placement table 7 on which surgical instruments are placed with the camera 1. The image taken by the camera 1 is sent to the computer 3 for detection of the small steel articles by image processing.

Figure 2:
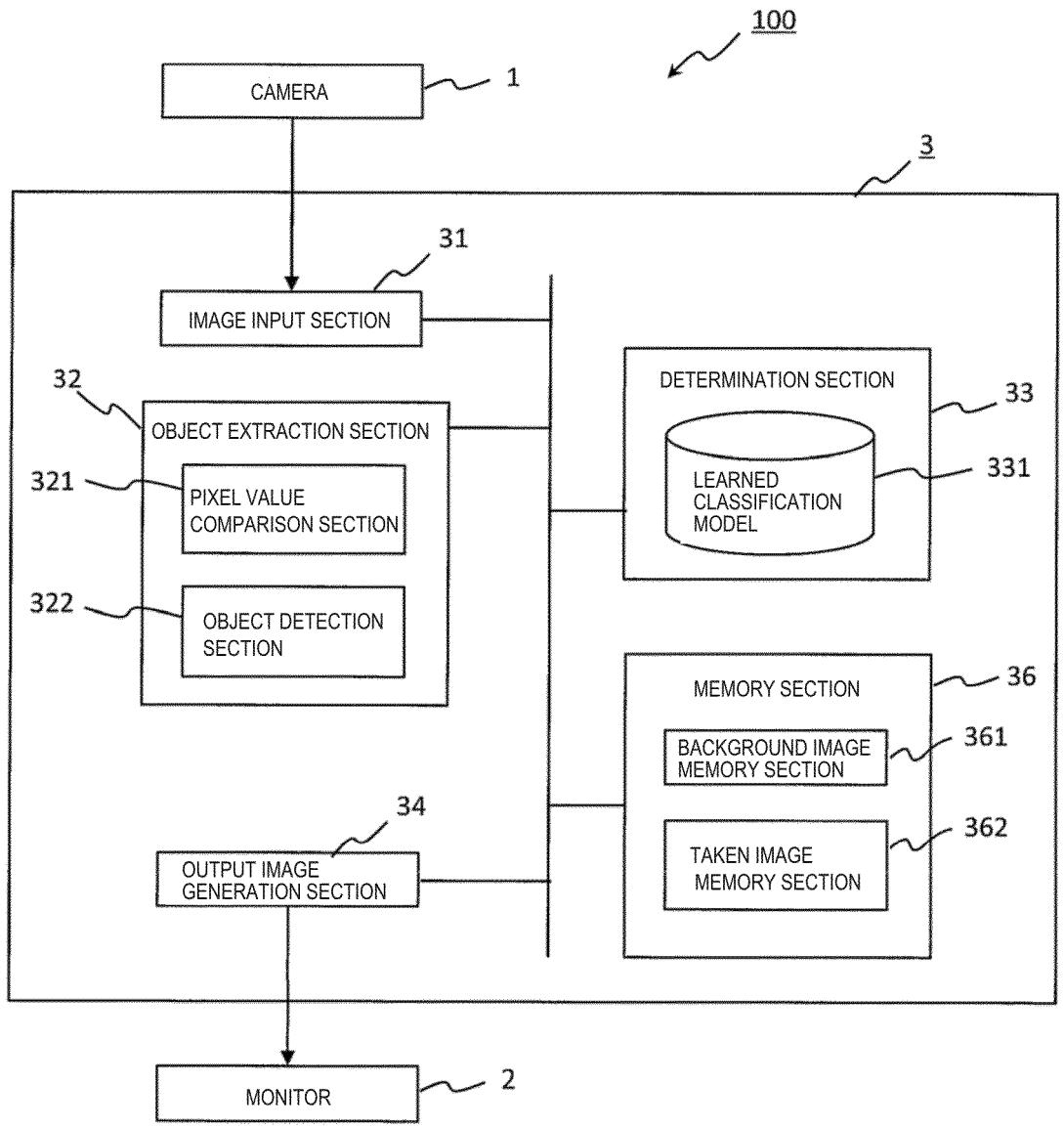
FIG. 2 is a block diagram schematically illustrating a functional configuration of the surgical instrument detection system according to the first embodiment.

FIG. 2 is a block diagram illustrating the functional configuration of the surgical instrument detection system 100. It should be noted that the block diagram illustrated in FIG. 2 conceptually illustrates the functions of the surgical instrument detection system by classifying them into blocks and that each block does not have to be actually implemented as individual hardware. It is possible to achieve each block by executing a predetermined program by a CPU of the computer 3.

As illustrated in FIG. 2, the surgical instrument detection system 100 includes an image input section 31 to input an image taken by the camera 1, an object extraction section 32 to clip an image of an object that is highly probably a small steel article from the input image, a determination section 33 to determine the kind of the small steel article from the object image clipped by the object extraction section 32, an output image generation section 34 to generate a display image indicating the result of determination by the determination section 33, and a memory section 36 to store data used for the process by the above sections.

Figure 3:
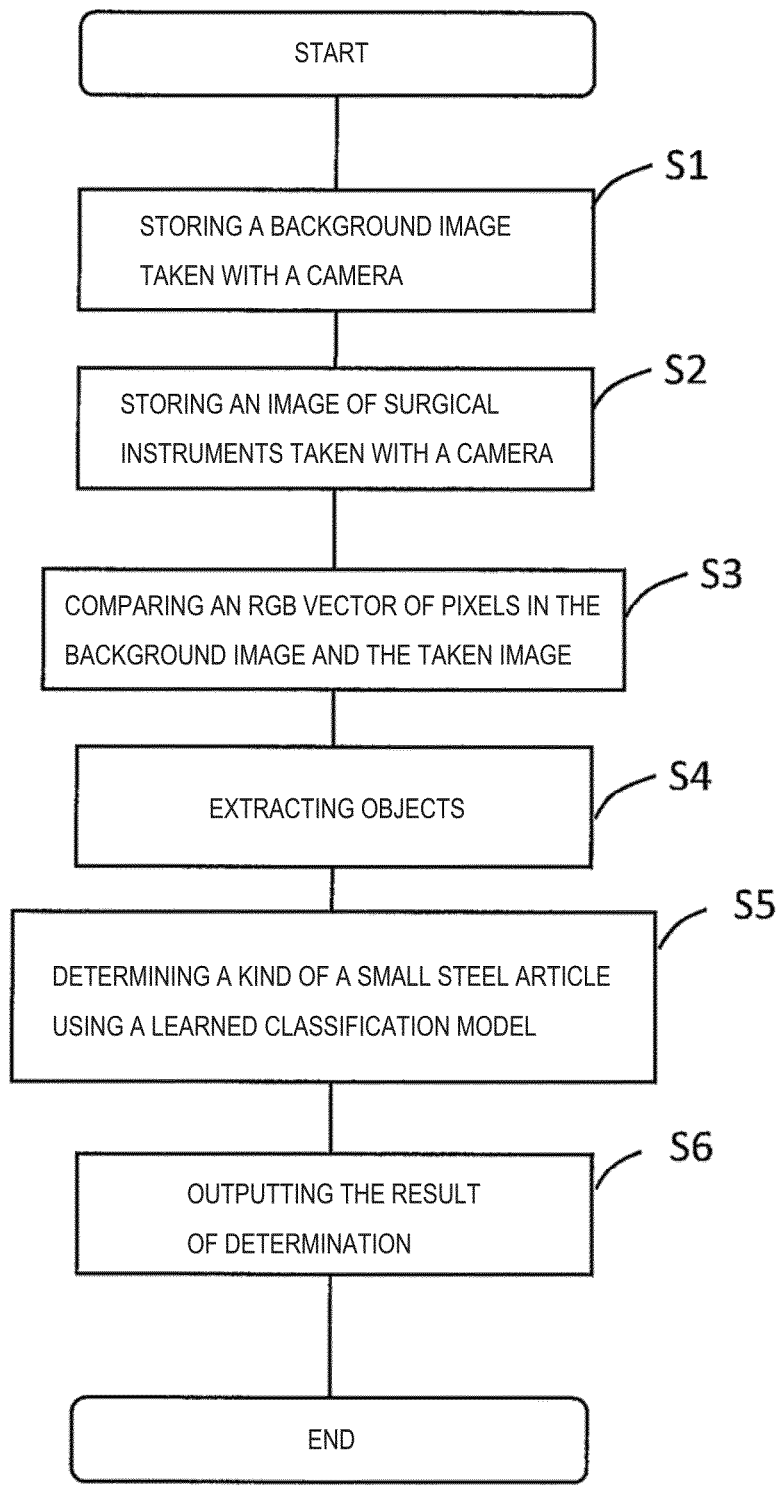
FIG. 3 is a flow chart illustrating a process flow by the surgical instrument detection system according to the first embodiment.

A procedure by each of the above section is described with reference to the flow chart in FIG. 3.

In the present embodiment, the object extraction section 32 performs pixel value comparison process to clip an image of an object that is highly probably a small steel article. Accordingly, in the present embodiment, an image of the instrument placement table 7 is taken with the camera 1 before placing surgical instruments to be used as a background image for reference. A sterilized sheet is generally spread on the instrument placement table 7 to arrange surgical instruments thereon. The background image taken before arranging the surgical instruments thus includes an image of the sterilized sheet only. The image input section 31 stores the background image taken with the camera 1 in a background image memory section 361 in the memory section 36 (S1).

Figure 4:
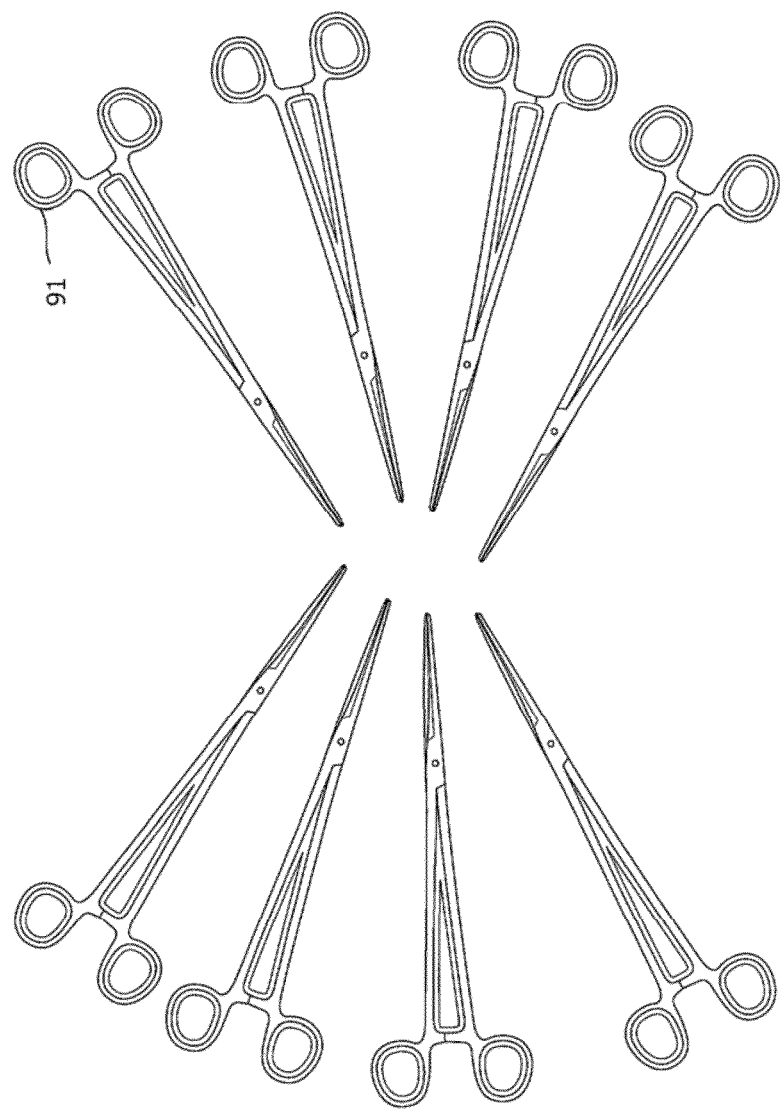
FIG. 4 is a schematic diagram illustrating an example of output to a monitor.

Then, when instruments used in surgery are set on the instrument placement table 7, an image of the instrument placement table 7 is again taken with the camera 1. The image thus taken is temporarily stored in a taken image memory section 362 in the memory section 36 by the image input section 31 (S2). As illustrated in FIG. 4, the taken image is displayed on the monitor 2 by the output image generation section 34. In the example of FIG. 4, an image is taken where eight pairs of forceps 91 are arranged on the instrument placement table 7.

The object extraction section 32 includes a pixel value comparison section 321. The pixel value comparison section 321 reads the background image and the taken image described earlier from the memory section 36 to compare an RGB vector of pixels included in each image (S3). The object extraction section 32 further includes an object detection section 322. The object detection section 322 determines an area composed of pixels having an angle made by the RGB vectors of both the background image and the taken image or a difference in vector magnitudes of them greater than a predetermined threshold as an object of a small steel article (S4). The taken image memory section 362 gives a flag indicating the object to the pixels constituting the object among the pixels included in the taken image.

Figure 5:
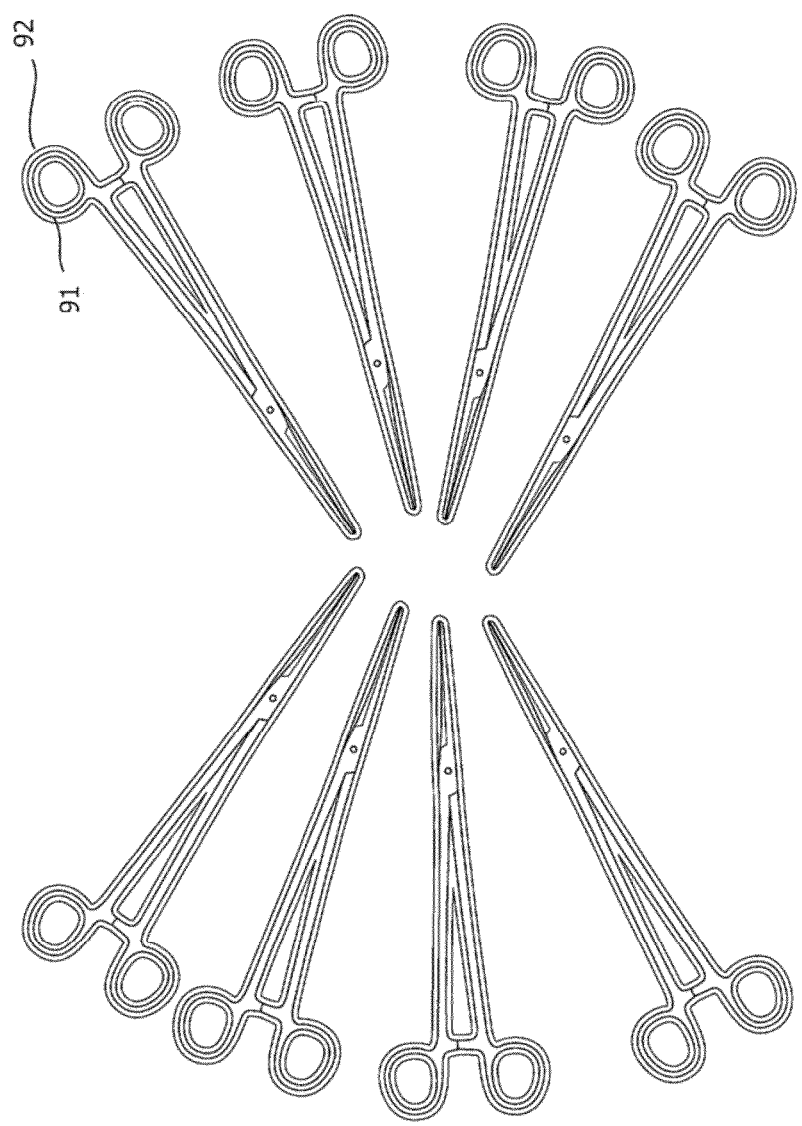
FIG. 5 is a schematic diagram illustrating another example of output to the monitor.

As illustrated in FIG. 5, the result of object extraction may be displayed on the monitor 2. In the example illustrated in FIG. 5, an object border 92 is displayed around each of the eight pairs of forceps 91 detected as the objects from the taken image.

When the process by the object extraction section 32 is completed, the determination section 33 determines which small steel article the extracted object corresponds to using a learned classification model 331 to which deep learning is applied (S5).

The learned classification model 331 is generated by learning many images of obtained by photographing various small steel articles. The small steel articles may be classified based on features such as the entire or partial shape and color. A change in the direction of light incident to such a small steel article greatly changes the brightness due to shades and mirror reflection, often affecting the recognition accuracy. The images for learning are thus preferred to be taken by variously changing the conditions of light incident to the small steel article.

The determination section 33 inputs each object image clipped by the object extraction section 32 to the learned classification model. The learned classification model decides which small steel article the object image corresponds to based on the features included in the input object image and outputs the result of decision together with probability of the decision. The probability of the decision is a value indicating the likelihood that the object image corresponds to the small steel article.

When the probability of the decision to the individual object image is greater than a predetermined value (e.g., 90%), the determination section 33 outputs data indicating the kind of small steel article output from the learned classification model as the result of determination for the object image to the output image generation section 34. Meanwhile, when the probability of the decision is the predetermined value or less, the determination section 33 outputs "unknown" as the result of determination for the object image to the output image generation section 34.

Figure 6:
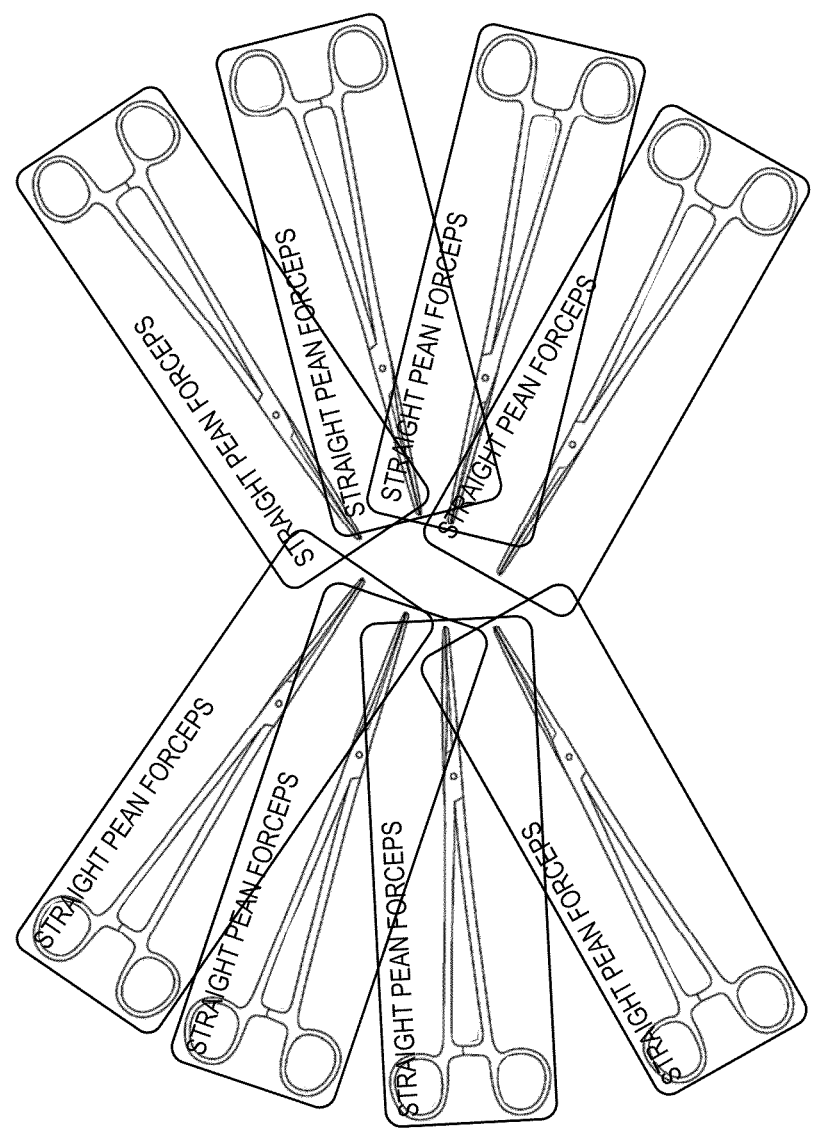
FIG. 6 is a schematic diagram illustrating a still another example of output to the monitor.

The output image generation section 34 generates an image to be output to the monitor 2 based on the result of determination received from the determination section 33 (S6). As illustrated in FIG. 6 for example, the output image generation section 34 generates an image containing a line surrounding each object and a text (character string) representing the result of determination and displays it on the monitor 2 overlaid on the taken image. At this point, if there is an object output as unknown or falsely recognized, a user manually corrects the result of determination and fix it. The result is fed back to the learned classification model, thereby allowing update of the model and improvement in recognition accuracy.

For example, Pean forceps can be classified by the shape at the tip end (straight/curved) and thus they are displayed with a text, such as "straight Pean forceps" or "curved Pean forceps". In the example of FIG. 6, all object images are determined as "straight Pean forceps".

As just described, the surgical instrument detection system 100 in the present embodiment clips the object images of the small steel articles from the image taken with the camera 1 and uses the learned classification model to each object image for automatic determination of the kinds of small steel articles. This allows accurate determination of the kinds of small steel articles without having to apply special processing, such as optically readable symbols, to the small steel articles.

Second Embodiment

A surgical instrument detection system 200 according to the second embodiment has, in addition to the surgical instrument detection system according to the first embodiment, a function of checking whether all small steel articles are complete after surgery.

Figure 7:
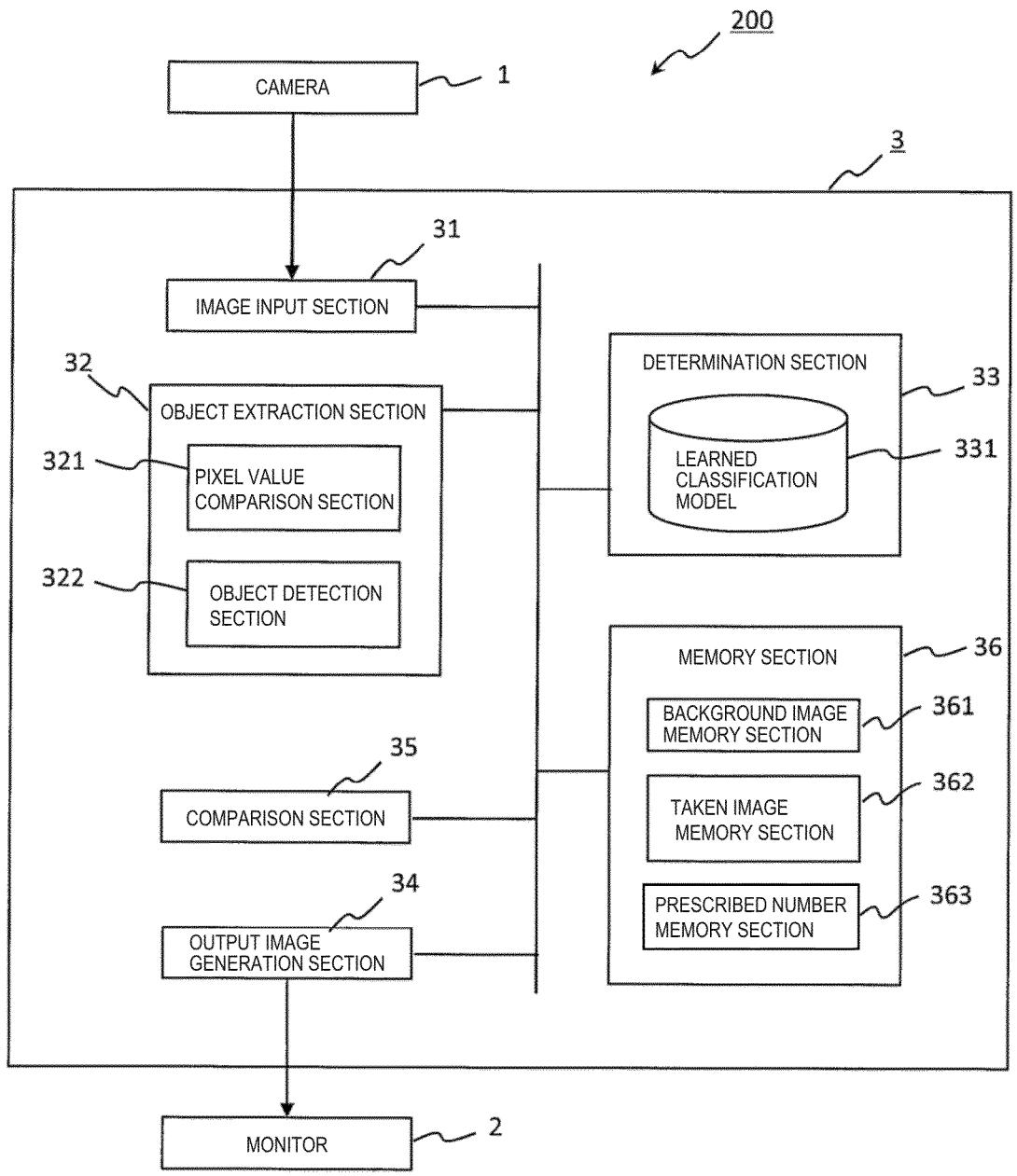
FIG. 7 is a block diagram schematically illustrating a functional configuration of a surgical instrument detection system according to a second embodiment.

As illustrated in FIG. 7, the surgical instrument detection system 200 thus further includes a comparison section 35. In the present embodiment, after surgery, collected small steel articles are placed on the instrument placement table 7 to be photographed with the camera 1 and, similar to the first embodiment, the kinds and number of the small steel articles included in the taken image are detected. The comparison section 35 compares the kinds and number of small steel articles before and after surgery to detect the excess or deficiency.

In the surgical instrument detection system 200, the memory section 36 further includes a prescribed number memory section 363 to memorize the kinds and number of small steel articles before surgery. That is, the prescribed number memory section 363 memorizes the kinds of small steel articles prepared for use in surgery and the number for each kind. The small steel articles to be used are arranged on the instrument placement table 7 before surgery to be photographed with the camera 1 and the kinds and number of the small steel articles determined by the determination section 33 are preferably memorized in the prescribed number memory section 363. Alternatively, without performing automatic detection by the system, the kinds and number of small steel articles to be used may be input using the keyboard 4 and the mouse 5.

Figure 8:
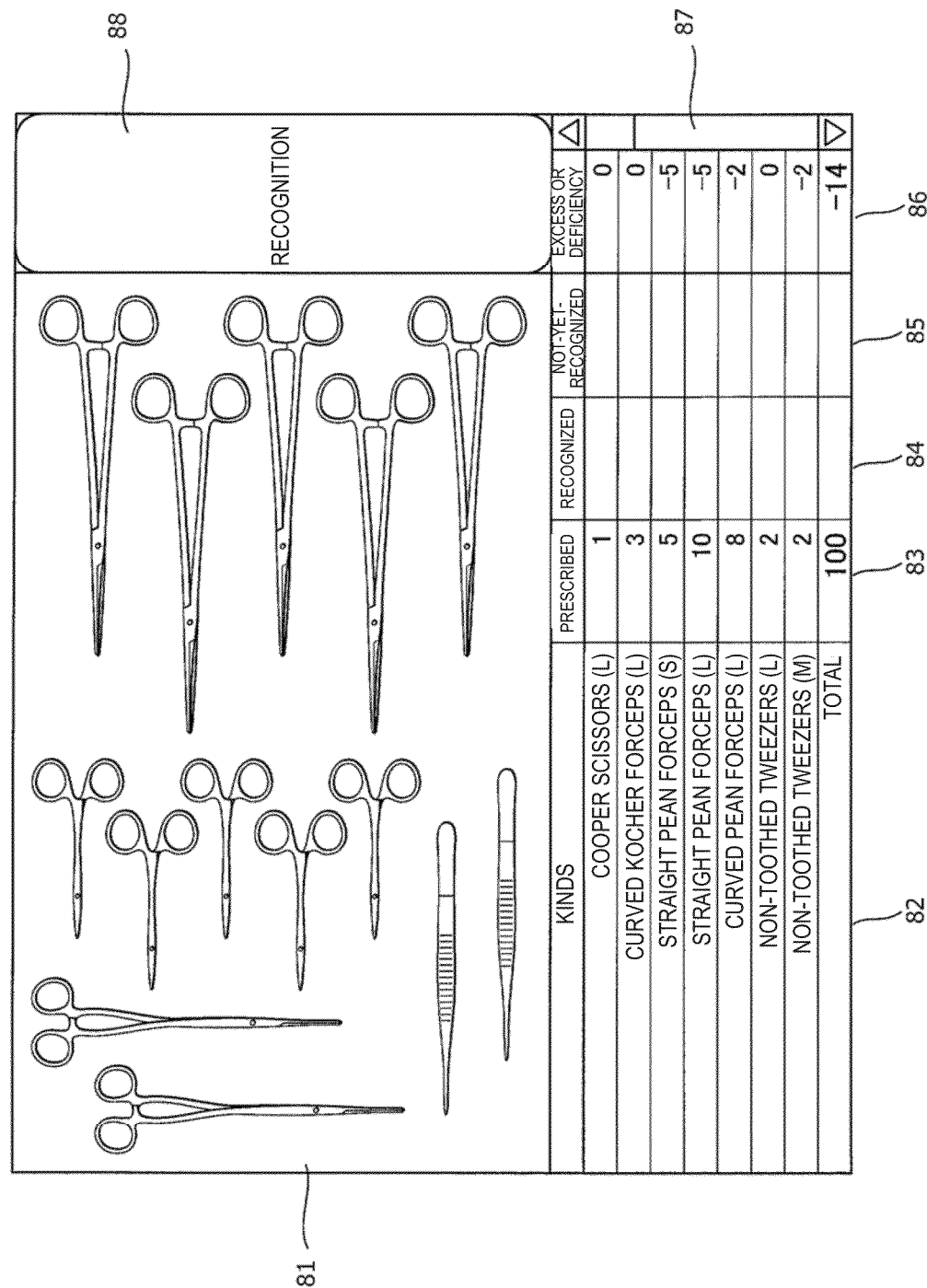
FIG. 8 is a schematic diagram illustrating an example of output to the monitor.
Figure 9:
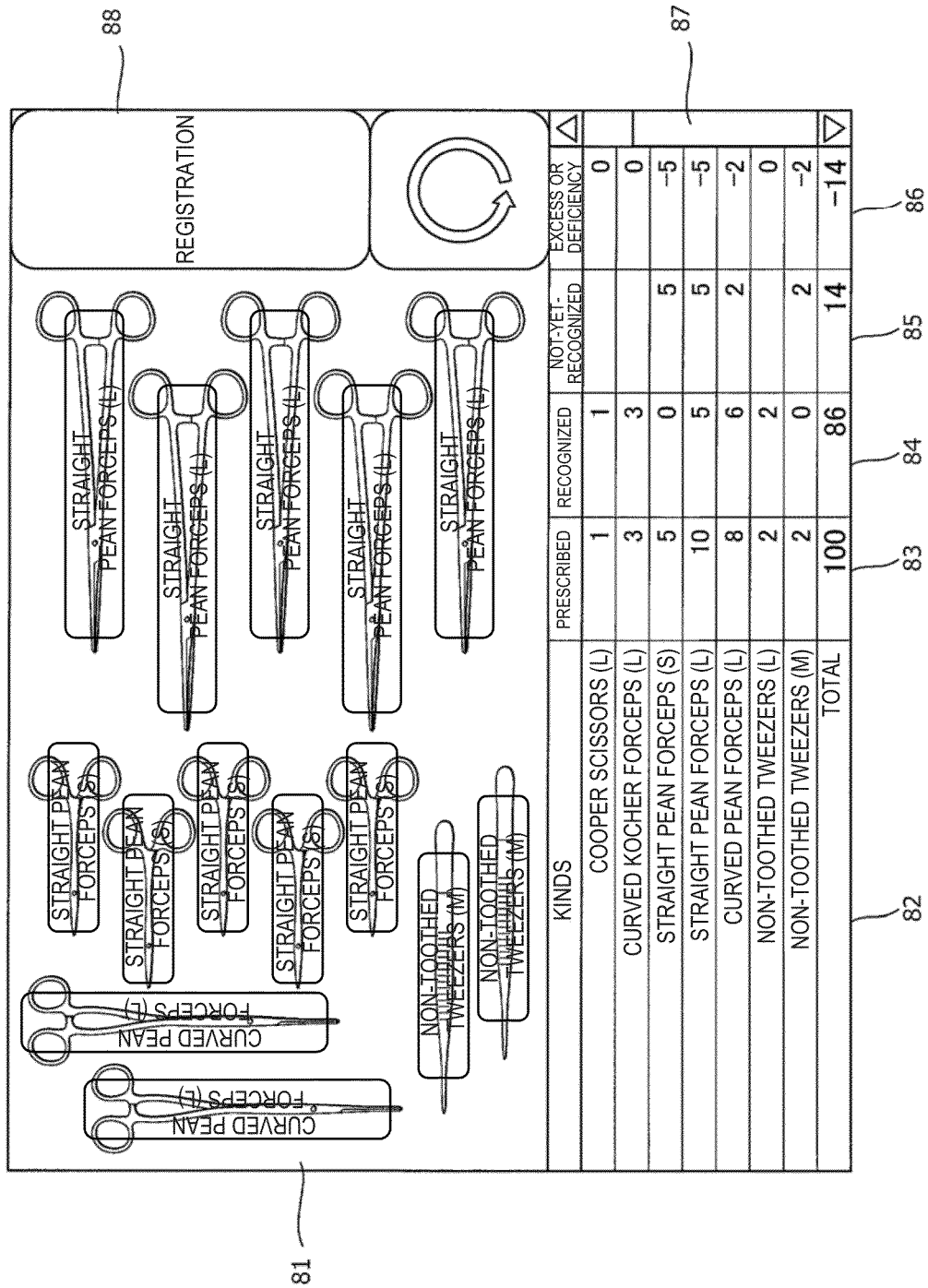
FIG. 9 is a schematic diagram illustrating another example of output to the monitor.

FIGS. 8 and 9 illustrate examples of a screen displayed on the monitor 2 in the surgical instrument detection system 200. FIG. 8 is an example of a screen displayed on the monitor 2 after small steel articles arranged on the instrument placement table 7 are photographed by the camera 1 after surgery. The screen exemplified in FIG. 8 displays a taken image display area 81, an instrument kind display field 82, a prescribed number display field 83, a recognized number display field 84, a not-yet-recognized number display field 85, an excess or deficiency number display field 86, a scroll bar 87, and a control button 88.

In the instrument kind display field 82, the kinds of small steel articles are displayed. In the prescribed number display field 83, the number of small steel articles before surgery is displayed for each kind based on the data memorized in the prescribed number memory section 363. In the recognized number display field 84, the not-yet-recognized number display field 85, and the excess or deficiency number display field 86, nothing is displayed at this point. On the control button 88, a command of "recognition" is displayed. When an operator clicks the control button 88 after the image taken by the camera 1 is displayed in the taken image display area 81, the process by the object extraction section 32 and the determination section 33 are started.

Then, as illustrated in FIG. 9, in the taken image display area 81, the kind of small steel article is displayed by text overlaid on each object of the small steel article detected from the taken image. At this point, a command of "registration" is displayed on the control button 88. In the not-yet-recognized number display field 85, the number of objects is posted that is determined to highly probably correspond to the kind by the determination section 33. If there is an object falsely recognized or decided as unknown, a user can correct the result of determination. Then, when the control button 88 is clicked, the result of determination for the not-yet-recognized objects is fixed and posted in the recognized number display field 84. In the excess or deficiency number display field 86, a value is displayed that is obtained by subtracting the number displayed in the recognized number display field 84 from the number displayed in the prescribed number display field 83. In the example of FIG. 9, the result of determination by the determination section 33 is displayed for the surgical instruments named as "straight Pean forceps (S)", "straight Pean forceps (L)", "curved Pean forceps (L)", and "non-toothed tweezers (M)". When recognition and registration of all small steel articles to be posted are completed with no problems, "O" is displayed in the excess or deficiency number display field 86.

As has been described, the present embodiment allows automatic comparison whether the kinds and number of small steel articles coincide before and after surgery by image recognition. It is thus possible to provide a system to automatically check if any small steel article is left in the patient's body without applying special processing to the small steel articles.

Third Embodiment

Figure 10:
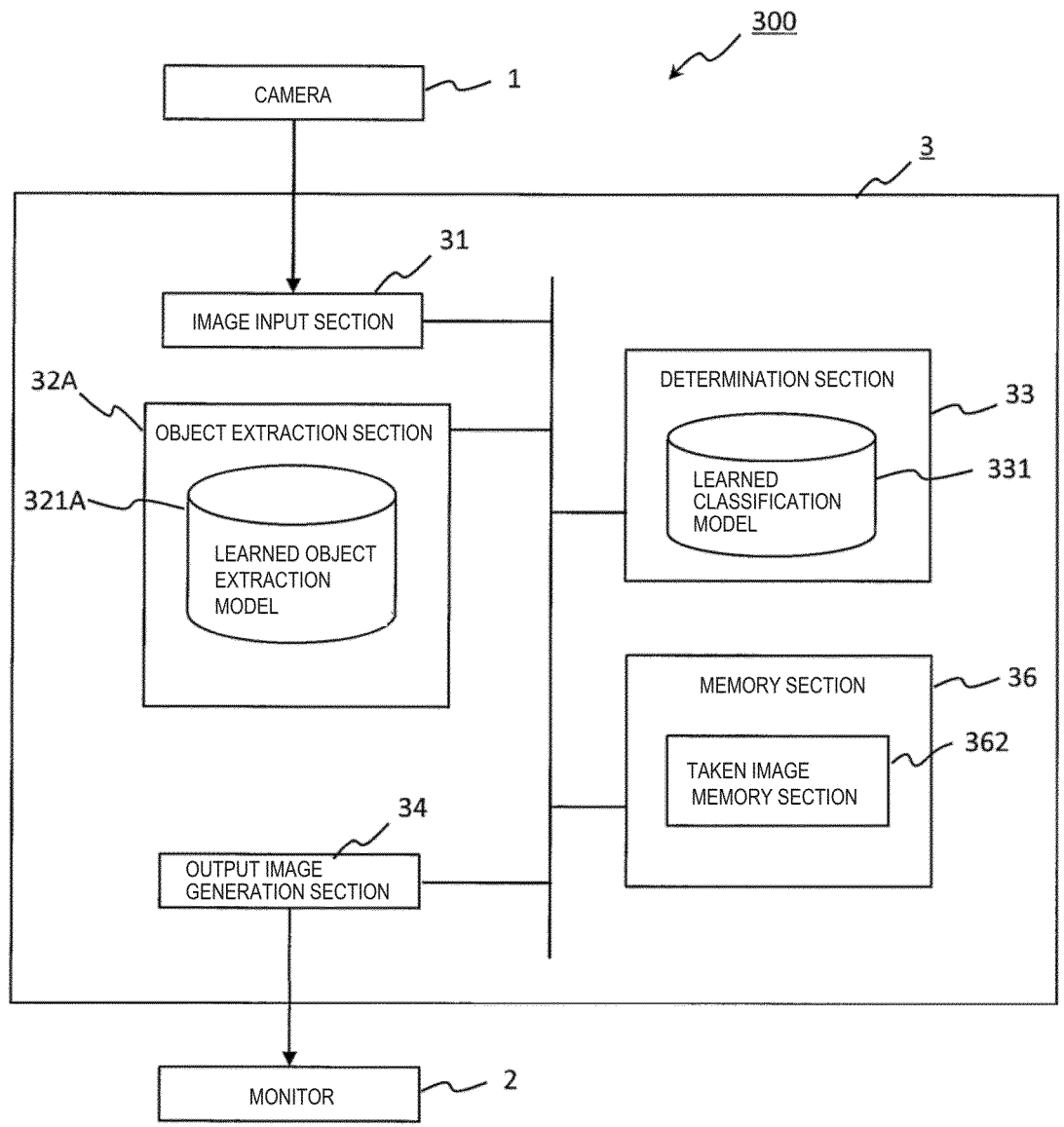
FIG. 10 is a block diagram schematically illustrating a functional configuration of a surgical instrument detection system according to a third embodiment.

A surgical instrument detection system 300 according to the third embodiment includes, as illustrated in FIG. 10, an object extraction section 32A instead of the object extraction section 32 in the first embodiment. The object extraction section 32A extracts an object image that is highly probably a small steel article using a learned object extraction model 321A to which deep learning is applied. It is possible to obtain such a learned object extraction model by learning many images of small steel articles placed on a sterilized sheet on the instrument placement table 7.

That is, the learned object extraction model is, different from the learned classification model used to decide the kinds of small steel articles, a learning model to determine whether a predetermined pixel (or a pixel area) is a part of an image of a small steel article or the background (sterilized sheet).

As just described, the present embodiment is different from the first embodiment in that the learned model is used for clipping of an object image as well.

In the present embodiment, photographing of the background image only is not required different from the first embodiment. In addition, use of a sufficiently learned model as the learned object extraction model allows accurate clipping of an object image.

The object extraction section 32A may be provided instead of the object extraction section 32 in the second embodiment.

Fourth Embodiment

Figure 11:
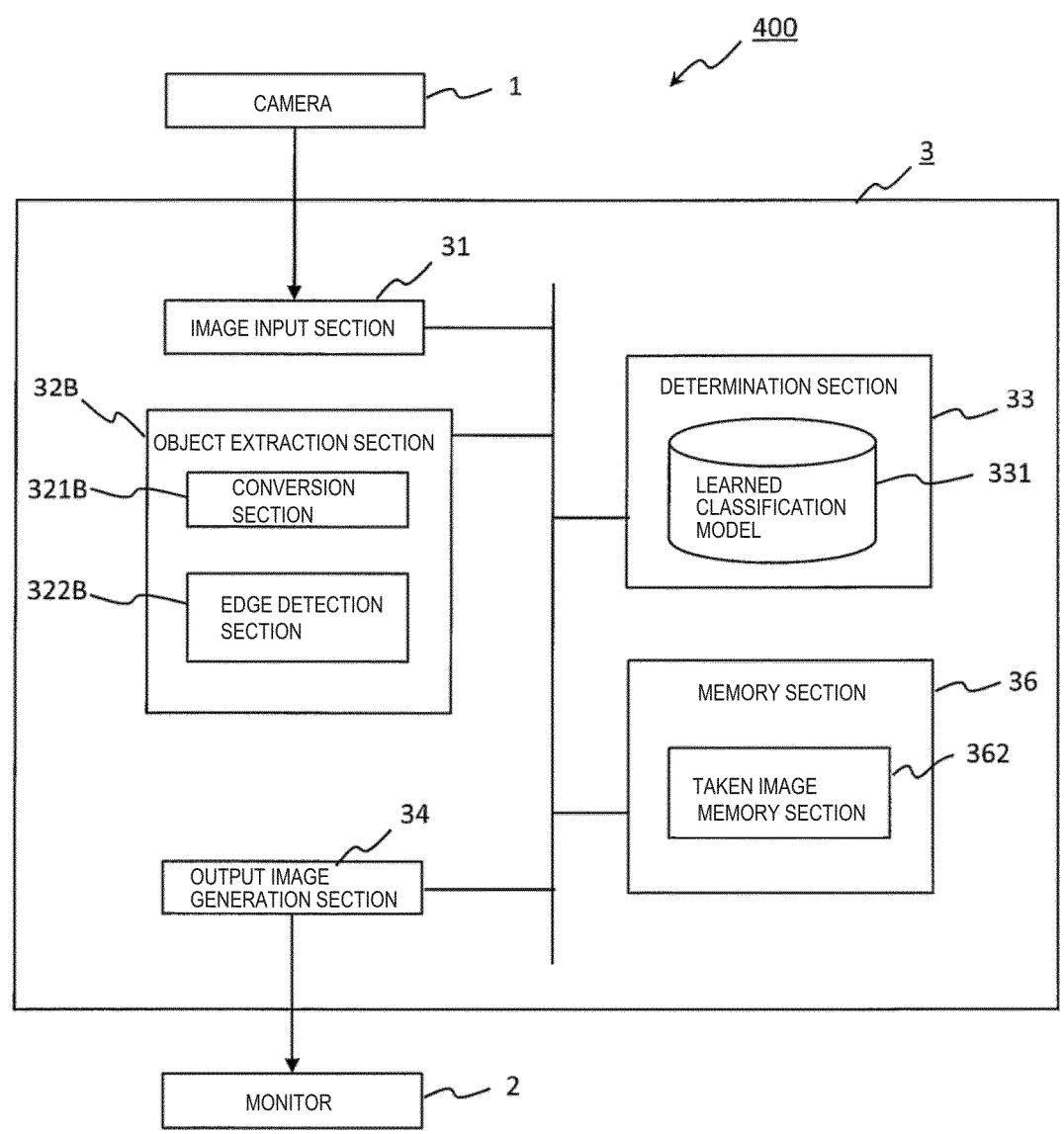
FIG. 11 is a block diagram schematically illustrating a functional configuration of a surgical instrument detection system according to a fourth embodiment.

A surgical instrument detection system 400 according to the present embodiment includes, as illustrated in FIG. 11, an object extraction section 32B instead of the object extraction section 32 in the first embodiment. The object extraction section 32B is provided with a conversion section 321B and an edge detection section 322B.

The object extraction section 32B detects an object taking advantage of low saturation in the HSV color space, such as silver and black, of small steel articles in contrast of sterilized sheets used as a background that are generally blue. The conversion section 321B converts the RGB data of the input taken image to data in the HSV color space. The edge detection section 322B detects an edge (border) of an object based on hue and saturation data. The edge detection technique is not particularly limited because various such technique is conventionally known, and for example, the canny method may be used. The edge extraction based on the hue and saturation data after converting the RGB data to the data in the HSV color space allows suppression of the influence by shades due to a change in ambient light. This is because, although the brightness data in RGB and the lightness data in HSV are affected by shades, the hue and saturation are less likely to be affected by shades compared with them.

The object extraction section 32B may be provided instead of the object extraction section 32 in the second embodiment.

While some embodiments of the present invention are described above, embodiments of the present invention are not limited only to the specific examples above and may be variously modified. It is also possible to embody the present invention by appropriately combining the functions described in the respective embodiments above.

For example, although the surgical instrument detection system to particularly detect small steel articles among surgical instruments is described in the above embodiments, the present invention is also applicable to detection of, other than the small steel articles, light metal surgical instruments with a surface finish equivalent to the small steel articles or surgical instruments made of other materials such as carbon or resins.

In the above description, the embodiments of the surgical instrument detection system are described as a system implemented in a server or a computer. It should be noted that embodiments of the present invention include a computer program and a storage medium storing the same to cause a general-purpose server or a computer to achieve the functions of each block described above.

That is, all or part of the process by each functional block in the above embodiments may be achieved by a program. Then, all or part of the process by each functional block in the above embodiments is performed by a central processing unit (CPU) in the computer. As an option, it is also possible to use a coprocessor, such as a graphics processing unit (GPU), a tensor processing unit (TPU), and a field programmable gate array (FPGA). The program to perform each process is stored in a memory device, such as a hard disk and a ROM, and read by the ROM or a RAM for execution.

Each process in the above embodiments may be achieved by hardware or by software (including the cases where it is achieved together with an operating system (OS), middleware, or a predetermined library). It may be achieved by process in combination of software and hardware.

The order to execute the processing method in the above embodiments is not limited to the description of the above embodiments and the order of execution may be changed without departing from the spirit of the invention.

The scope of the present invention includes a computer program causing a computer to execute the method described earlier and a computer readable storage medium having the program stored therein. Examples of the computer readable storage medium include flexible disks, hard disks, CD-ROMs, MOs, DVDs, DVD-ROMs, DVD-RAMs, Blu-ray discs (BD), and semiconductor memories.

The computer program is not limited to those stored in the above storage medium and may be transmitted via electrical communication lines, wireless or wired communication lines, networks including the internet, and the like.

REFERENCE SIGNS LIST

1: Camera, 2: Monitor, 3: Computer, 4: Keyboard, 5: Mouse, 6: Cart, 7: Instrument Placement Table, 31: Image Input Section, 32: Object Extraction Section, 33: Determination Section, 34: Output Image Generation Section, 35: Comparison Section, 36: Memory Section, 100, 200, 300, 400: Surgical Instrument Detection System

The invention claimed is:

1. A surgical instrument detection system, including:
an image input section to input an image taken by a camera;
an object extraction section to clip an object image of a surgical instrument from the input image;
a determination section to input the object image to a learned classification model and determine a kind of the surgical instrument together with probability of the decision based on features included in the object image; and
an output image generation section to generate an image representing the result and probability of determination by the determination section and output such image to a monitor, wherein
the determination section outputs data indicating the kind of the surgical instrument output from the learned classification model as the result of determination for the object image to the output image generation section when the probability of the decision to the individual object image is greater than a predetermined value, and outputs "unknown" as the result of determination for the object image to the output image generation section when the probability of the decision is the predetermined value or less; and
the surgical instrument detection system accepts correction of the result of the determination from a user, thereby updates the learned classification model if there is an object output as unknown or falsely recognized, wherein the learned classification model is updated in its actual operation.

2. The surgical instrument detection system of claim 1, wherein the output image generation section outputs an image representing the kind of the surgical instrument overlaid on the object image in the taken image.

3. The surgical instrument detection system of claim 1, wherein the object extraction section inputs the taken image to a learned object extraction model and clips the object image based on features included in the taken image.

4. The surgical instrument detection system of claim 1, wherein the object extraction section converts pixel data of the taken image to data in an HSV color space and clips the object image based on edge information on hue and saturation.

5. The surgical instrument detection system of claim 1, further comprising a comparison section to compare the kinds and number of surgical instruments after surgery with the kinds and number of surgical instruments before surgery, wherein
the output image generation section generates an image representing the result of comparison by the comparison section and outputs such image to the monitor.

6. A non-transitory computer readable storage medium comprising a program causing a processor of a computer to execute surgical instrument detection, wherein
the surgical instrument detection comprises instructions for inputting an image taken by a camera;
clipping an object image of a surgical instrument from the input image;
determining, by inputting the object image to a learned classification model, a kind of the surgical instrument together with probability of the decision based on features included in the object image; and
generating an image representing the result and probability of determination and outputting such image to a monitor, wherein
data indicating the kind of the surgical instrument output from the learned classification model as the result of determination for the object image is utilized for the generating the image representing the result and probability of determination when the probability of the decision to the individual object image is greater than a predetermined value, and the learned classification model outputs "unknown" as the result of determination for the object image for the generating the image representing the result and probability of determination when the probability of the decision is the predetermined value or less, and
the surgical instrument detection accepts correction of the result of the determination from a user, thereby updates the learned classification model if there is an object output as unknown or falsely recognized, wherein the learned classification model is updated in its actual operation.

7. A surgical instrument detection method executed by a processor of a computer, the method comprising:
inputting an image taken by a camera;
clipping an object image of a surgical instrument from the input image;

determining, by inputting the object image to a learned classification model, a kind of the surgical instrument together with probability of the decision based on features included in the object image; and generating an image representing the result and probability of determination and outputting such image to a monitor, wherein data indicating the kind of the surgical instrument output from the learned classification model as the result of determination for the object image is utilized for the generating the image representing the result and probability of determination when the probability of the decision to the individual object image is greater than a predetermined value, and the learned classification model outputs "unknown" as the result of determination for the object image for the generating the image representing the result and probability of determination when the probability of the decision is the predetermined value or less, and the surgical instrument detection method accepts correction of the result of the determination from a user, thereby updates the learned classification model if there is an object output as unknown or falsely recognized, wherein the learned classification model is updated in its actual operation.

8. A surgical instrument detection system, including:

an image input section to input an image taken by a camera;

an object extraction section to clip an object image of a surgical instrument from the input image;

a determination section to input the object image to a learned classification model and determine a kind of the surgical instrument together with probability of the decision based on features included in the object image; and an output image generation section to generate an image representing the result and probability of determination by the determination section and output such image to a monitor, wherein the surgical instrument detection system accepts correction of the result of the determination from a user, thereby updates the learned classification model, the object extraction section clips the object image based on comparison of a color space vector for each pixel in a background image and the taken image.

* * * * *